United States Patent
Jin-Ya et al.

(10) Patent No.: US 6,174,486 B1
(45) Date of Patent: Jan. 16, 2001

(54) METHOD FOR HEAT-SETTING SPANDEX-CONTAINING GARMENTS

(75) Inventors: Tateo Jin-Ya, Nara Prefecture; Hirofumi Matsuda, Toyonaka, both of (JP)

(73) Assignee: DuPont Toray Co. Ltd., Tokyo (JP)

( * ) Notice: Under 35 U.S.C. 154(b), the term of this patent shall be extended for 0 days.

(21) Appl. No.: 09/140,382

(22) Filed: Aug. 26, 1998

Related U.S. Application Data

(63) Continuation-in-part of application No. 09/029,917, filed as application No. PCT/US96/14709 on Sep. 9, 1996, now abandoned.

(30) Foreign Application Priority Data

Sep. 11, 1995 (JP) .................................................... 7-259202

(51) Int. Cl.[7] .......................... B29C 35/08; B29C 35/02; B29C 35/04; B29C 61/00; B29C 71/02
(52) U.S. Cl. ..................... 264/327; 264/235; 264/346; 264/481; 264/485; 264/492; 264/493; 264/519; 425/174.4; 425/446; 425/403; 425/393; 2/239; 2/409
(58) Field of Search ..................... 264/230, 235, 264/327, 346, 479, 481, 485, 492, 493, 519; 425/174.4, 446, 445, 403, 393; 2/409, 239

(56) References Cited

U.S. PATENT DOCUMENTS

| | | | |
|---|---|---|---|
| 1,907,511 | * 5/1933 | Davies | 264/230 |
| 4,025,597 | * 5/1977 | Sawamoto | 264/138 |
| 4,180,065 | * 12/1979 | Bowen | 128/165 |
| 4,526,732 | * 7/1985 | Kakii et al. | 264/2.7 |
| 4,645,629 | * 2/1987 | Stern | 264/23 |
| 4,783,293 | * 11/1988 | Wellerhaus et al. | 264/40.6 |
| 5,108,277 | * 4/1992 | Dixon | 425/72.1 |

FOREIGN PATENT DOCUMENTS

| | | |
|---|---|---|
| 719795 | 12/1954 | (GB) . |
| 279403 | 12/1991 | (JP) . |
| 287801 | 12/1991 | (JP) . |
| 18102 | 1/1992 | (JP) . |

OTHER PUBLICATIONS

Patent Abstracts of Japan, vol. 16, No. 351 (C–0968), Jul. 29, 1992 & JP,A,04 108101 (Toyobo Co. Ltd.), Apr. 9, 1992.
Patent Abstracts of Japan, vol. 16, No. 98 (C–0918), Mar. 11, 1992 & JP,A,03 279403 (Gunze Ltd.), Dec. 10, 1991.

* cited by examiner

Primary Examiner—Jan H. Silbaugh
Assistant Examiner—Michael I. Poe
(74) Attorney, Agent, or Firm—George A. Frank

(57) ABSTRACT

A method of heat-setting garments by boarding the garment and subjecting it to preselected temperatures that are different for different parts of the garment and an apparatus for carrying out this method are provided.

4 Claims, 1 Drawing Sheet

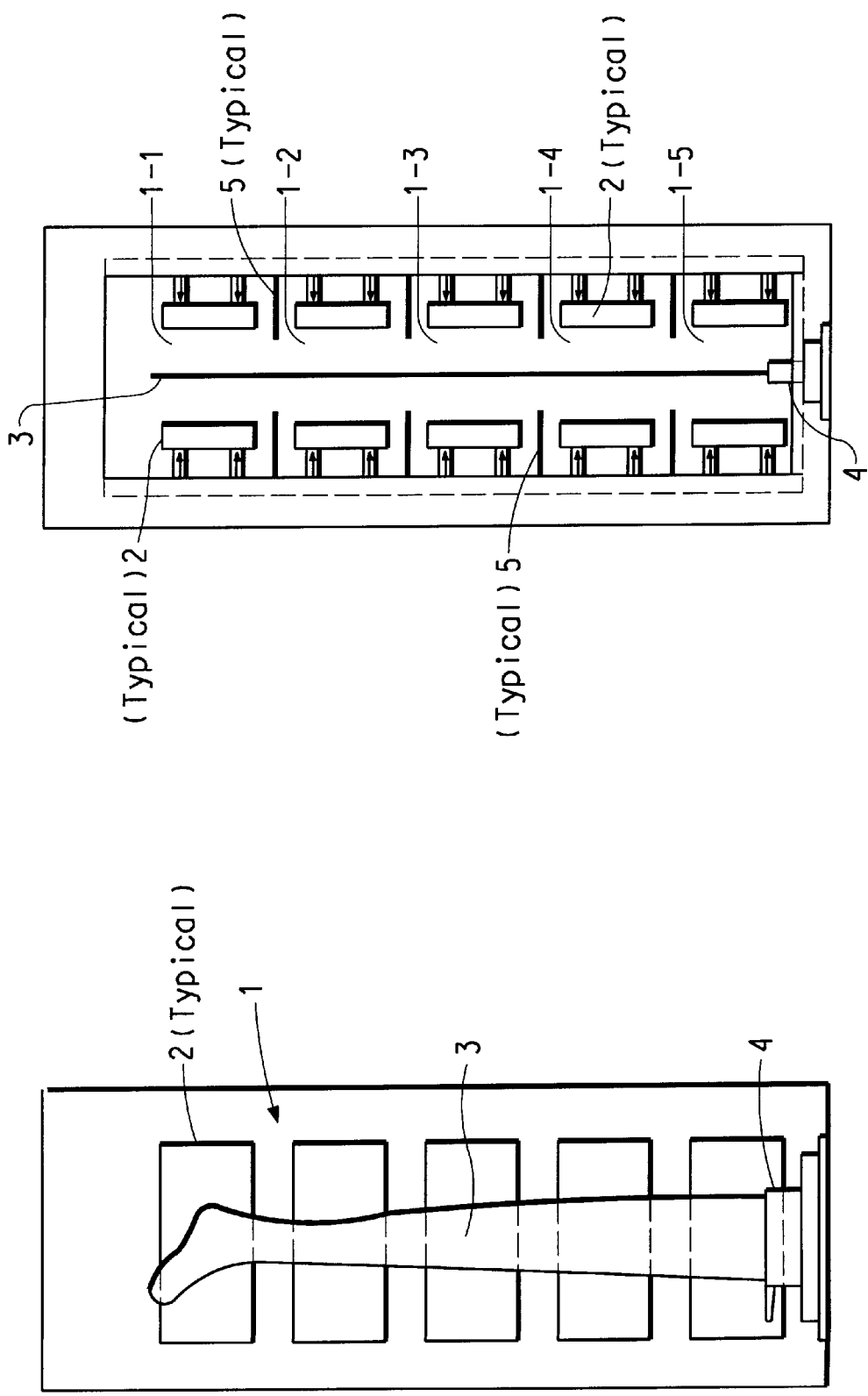

METHOD FOR HEAT-SETTING SPANDEX-CONTAINING GARMENTS

CROSS-REFERENCE TO RELATED APPLICATIONS

This application is a continuation-in-part of PCT/US96/14709, filed Sep. 11, 1996, U.S. Application Ser. No. 09/029,917, filed Mar. 10, 1998 now abandoned.

BACKGROUND OF THE INVENTION

This invention pertains to a method of heat-setting a garment by boarding the garment and subjecting it to preselected thermal conditions that are different for different parts of the garment.

DISCUSSION OF BACKGROUND ART

Methods have been proposed to modify stockings so that the pressure felt by different parts of a leg of a wearer are different. Japanese Kokai Patent No.'s Hei 3(1991)-287801, No. Hei 3(1991)-279403 and No. Hei 4(1992)-18102 each discloses a method for making stockings in which the knitting is changed for different parts of the stocking so that mesh size, yarn denier, and/or length of yarn per course is different and correspond to different parts of a wearer's leg. As a result, the pressure experienced by the wearer is different for different parts of the leg. However, such methods require complex knitting procedures in order to vary the stitch density (mesh size), length of yarn fed per course, and yarn denier.

A variety of methods have also been proposed to board and heat-set garments, including stockings. British Patent Number 719,795 discloses an apparatus for heat-setting stockings which do not contain spandex by passing them through a tunnel-like oven on an endless conveyor. Baffle plates are disclosed to direct the hot air onto the welt (knitted non-raveling edge) of the stocking. However, this is an imprecise method in that the hot air merely enters at that point and is not prevented from affecting the rest of the stocking.

Japanese Kokai Patent No. Hei 4(1992)-108181 discloses a method of exposing different parts of a stocking to UV radiation in addition to uniformly heating the entire stocking in order to adjust the stretch in different parts of the stocking. However, this method can result in undesirable deterioration of the fibers in parts of the stocking that have been exposed to the radiation.

A versatile and simple method of making stockings so that the pressure on the wearer's leg is different in several parts of the leg is still needed, as is a practical apparatus for carrying out such method.

SUMMARY OF THE INVENTION

The method of the present invention for heat-setting a garment containing spandex comprises the steps of:

mounting the garment comprising a plurality of garment parts on a boarding form;

heating the mounted garment by subjecting the garment to a plurality of preselected elevated temperatures corresponding spatially to the garment parts; and removing the garment so heat-set from the form.

The apparatus of the present invention for heat-setting garments comprises:

at least one chamber;

a plurality of heating zones within the chamber;

a plurality of heating means, each heating means being positioned in a heating zone; and a boarding form for mounting the garment, the form being supported within the chamber so that the heating zones correspond spatially to the garment parts.

BRIEF DESCRIPTION OF THE DRAWINGS

FIG. 1 shows a side view (boarding form in profile) and FIG. 2 shows a front view (boarding form on edge) of one embodiment of the boarding apparatus of the present invention.

DETAILED DESCRIPTION OF THE INVENTION

As used herein, "spandex" means a manufactured fiber in which the fiber-forming substance is a long chain synthetic elastomer comprised of at least 85% by weight of a segmented polyurethane. "Part" of a garment means a section of the garment attached to another section of the garment, each section being associated with a corresponding body part of a wearer, for example foot, calf, thigh, arm, back, and the like.

Knit garments are often heat-set under tension to stabilize their dimensions. In the case of garments containing spandex, such heat-setting can generally be performed at temperatures in the range of about 40° C. to 300° C., preferably 60° C. to 200° C. When the garment is a pair of stockings, such heat-setting can be performed on a boarding form in the shape of a leg. Stockings, such as pantyhose, which exert different pressures on different parts of the body, such as the foot (toes and ankle), calf, knee, thigh and abdomen, are more comfortable to the wearer.

By means of the present invention, garments with excellent comfort, feel and fatigue alleviating effects can be obtained from a greige knit fabric made with a relatively simple knitting design and without adopting complicated knitting methods. Because of the resulting high knitting productivity, cost can be reduced markedly. In the past, the part of the garment where the pressure was intended to be low has been realized by increasing the amount of yarn fed to the knitting machine, changing the yarn denier, and/or changing the knit mesh size (stitch density). It has now been found that substantially the same result can be realized by raising the level of heat-setting by selectively increasing the temperature to which each such part of a garment is exposed. Conversely, where in the past the part of the garment where the pressure was intended to be high has been realized by, for example, decreasing the amount of yarn feed on the knitting machine, substantially the same result can now be realized by lowering the level of heat-setting by lowering the temperature to which such part is exposed.

The method and apparatus of the present invention can be applied to garments having substantially the same mesh size throughout the garment. Such garments can include brassieres, girdles, pants, shirts, gloves, pantyhose, and stockings. The length of yarn fed into each course and the tension with which the yarn is knit determine the mesh size in each course. When the mesh size (stitch density) or length of yarn fed is substantially the same throughout the garment, the method and apparatus of this invention can be used to alter the compressive force exerted by different parts of the garment when it is worn.

This way, knitting adjustments can be significantly reduced, because even when the mesh size or amount of yarn fed is changed for various parts of the garment (for example a stocking or pantyhose), the method and apparatus of the invention can be combined with such knitting changes to further adjust and optimize the resulting compressive force, thereby significantly reducing the need for such changes.

For example, the pressure or binding force of stockings has traditionally been adjusted by varying the amount of yarn fed to the knitting machine in more than twenty steps in the lengthwise (wale) direction of the stockings. In contrast, by means of the method of this invention, a greige stocking of simplified knitting design, wherein the toe-to-lower calf part has substantially the same amount of yarn feed, the upper calf-to-lower thigh part has a substantially constant but proportionally increased amount of yarn feed (compared to the toe-to-lower calf), and the thigh-to-abdomen part has substantially the same amount of yarn feed but at a higher level than the other parts, can be heat-set by varying the heat-setting conditions in the lengthwise (wale) direction according to this invention to obtain the requisite pressure, even though only three knitting changes are used. The knitting complexity is thus considerably reduced compared to the traditional method, but the resulting stockings are comparable in the pressure exerted at different parts of the leg.

Use of yarns having higher heat-set efficiency requires even fewer adjustments of the knitting process so that a tubular knit stocking can be manufactured with substantially the same amount of yarn feed from toe to abdomen.

In the present method, a spandex-containing garment to be heat-set is mounted on a boarding form (for example a leg form), and the mounted garment is exposed to a plurality of preselected temperatures. At least two, preferably at least three, and more preferably at least four different preselected temperatures can be applied so that different parts of the garment experience different temperatures. The heat must be sufficient to heat-set spandex, but to differing extents depending on the temperature. As a result, the thermal histories of the different parts of the garment will be different, and the compressive force will also be different in various parts of the garment.

The temperatures can differ in the vertical direction of the garment (i.e. in the direction of wales of stockings) or in the horizontal direction (i.e., in the direction of courses in stockings). For most purposes, temperatures differing in the vertical direction of the garment are preferred, so that in the case of stockings or pantyhose the compressive force decreases in the order: foot, calf, knee, and thigh. Preferably, the pressure experienced by the wearer on the foot, calf, knee and thigh is adjusted to within a range of 40–57 grams-force per square centimeter ($gf/cm^2$), 27–47 $gf/cm^2$, 20–32 $gf/cm^2$, and 19–29 $gf/cm^2$, respectively.

Fibers in various parts of garments treated by the process of the present invention shrink by different percentages in boiling water as a result of their differing thermal histories, and their stress recovery from elongation is also different if they are taken from differing parts of a stocking which has been heat-set by the present method.

The garments, particularly stockings, processed by this method include those made from conventional knits. For instance, they can be made of a knitting yarn that contains spandex, polybutylene terephthalate fibers, polyesterether fibers, or polyester elastic fibers. The elastic fiber can be bare (100% elastic yarn), a combination (covered) elastic yarn that is made from non-elastic fibers such as polyamide, polyester, or cotton fibers over a core of elastic fibers, or mixtures of elastic fibers and non-elastic fibers. For stockings, the knitting yarn has a total denier (d) of 5–300, preferably 10–200. These yarns can be a mixture of heavy denier fibers and fine denier fibers, and the fibers with a fine denier can also include super-fine fibers with a single-fiber denier of 0.1 or less.

Heat-setting of garments can be by dry heat or wet heat, or a combination of the two. The heating means include electrothermal heaters, electron-beam heaters, infrared-ray heaters, steam, and hot water. Infrared-ray sources and far infrared sources (both of which provide dry heat) are preferred because more precise local heating of any garment part is possible.

Heat-setting can be performed at a temperature of about 40° C.–300° C., preferably 60° C.–200° C. The compressive force of the heat-set yarn varies with the type of heat used and, therefore, the temperature range must be changed depending on the type of heat and the part of the garment being heat-set. For instance, when heat-setting stockings, a temperature range of about 60° C.–150° C. is preferred when steam is used and a temperature range of about 80° C.–200° C. is preferred when dry heat is used. The preferred setting temperature for each part of the stockings when dry heat is used is about 100° C.–140° C. for the foot, 110° C.–150° C. for the calf, 130° C.–170° C. for the knee, and 150° C.–200° C. for the thigh.

A combination of wet-heat treatment and dry-heat treatment can also be employed. For instance, pre-treatment of stockings with wet heat, followed by dry-heat, affords stockings which can be heat-set and finished so that they feel softer.

Turning to FIG. 1, a side view of the apparatus of the present invention is shown with a boarding form 3 in profile, mounted on holder 4 inside chamber 1. Heat sources 2 are shown arranged so as to provide different temperatures to different parts of form 3.

FIG. 2 shows a front view of the apparatus with boarding form 3 shown on edge and mounted on holder 4. As in FIG. 1, heat sources 2 are mounted so that they apply heat to heating zones that are oriented in the course direction of the garment. Two heat sources are shown for each zone and are placed facing each other on either side of form 3. Sub-chambers 1-1, 1-2, 1-3, 1-4, and 1-5 correspond to the heating zones and are separated from each other by barriers 5 so that they are in no substantial thermal communication with each other.

The apparatus of this invention can heat each part of the stocking to be set as needed while limiting diffusion of heat between heating zones by using a barrier, for example a diaphragm, between the zones, the barrier being arranged so that it does not touch the stocking being heat-set. Thus at least two sub-chambers are formed within the main chamber, without the sub-chambers being in substantial thermal communication with other sub-chambers. Thus the apparatus can have several different and substantially independent zones oriented in the direction of horizontal and/or vertical rows, each zone corresponding spatially to a sub-chamber. The garments can be set on a form where the heat is precisely and finely varied at specific points between the zones corresponding to selected parts of the garment, or they can be set on a form where the different heat conditions vary more continuously from one zone to the next. It is preferred that there be several separate heating zones and corresponding heating means inside at least one chamber or housing. Each such heating means may comprise a pair of heat sources, preferably positioned on opposite sides of the boarding form. However, it is possible to use heating means that are separated in two or more separate chambers. As many heating zones and means as needed can be used to heat-set the garment as desired in accordance with the shape and function of the garment.

For stockings, the leg form can have a telescoping mechanism and a collapsing mechanism for reducing and increasing volume. This makes easier to perform the stretching-and-relaxation treatments that are useful in adjusting the force used during setting of the stockings. It also makes it easier to put the stocking onto the form and take it off the form after heat-setting.

In a preferred embodiment of the apparatus of the invention, the heat-setting device of this invention comprises at least three separate heating zones and corresponding sub-chambers arranged one above another along the length of a stocking board form and separated by a heat diffusion barrier between each zone. The barrier does not touch the stockings. A different temperature can be used in each sub-chamber. Dry heat is provided by infrared or far-infrared heat sources positioned in each sub-chamber.

The shape and structure of the apparatus and the heating zones can vary with the garment to be heat-set. Any shape and heat source can be used as long as it is capable of setting each part of the garment to be treated.

EXAMPLE

Covered yarn having a core of 15 d polyurethane elastic yarn covered with 12 d polyamide fibers was knitted on a pantyhose knitting machine. After pre-setting the knit for 20 minutes using steam at 100° C., the toes and seams of the knit were then sewed to make pantyhose. The pantyhose was then dyed beige with acid dye using a drum-dyeing device. The amount of yarn feed of the dyed pantyhose was 100 cm/horizontal row (or course) for the toe and the ankle and 130 cm/horizontal row (or course) for the thigh.

The dyed pantyhose was placed on a stainless steel leg form and the edges of the hip section of the pantyhose were fixed with an elastic band. This was then placed in the heat-setting apparatus, which had the following four sub-chambers in one chamber: a sub-chamber for the foot (including toes and ankle) in which the temperature was adjusted to 130° C., a sub-chamber for the calf in which the temperature was 150° C., a sub-chamber for the knee in which the temperature was 160° C., and a sub-chamber for the thigh in which the temperature was 170° C. The heating time was 2 minutes.

The pressure of the pantyhose on a leg form after heat-setting was 45 gf/cm$^2$ on the foot (toes and ankle), 35 gf/cm$^2$ on the calf, 25 gf/cm$^2$ on the knee, and 20 gf/cm$^2$ on the thigh. These values were determined from the compressive force of each part of the pantyhose on the form with a PS-B pressure sensor made by Kyowa Denkyo (Japan).

What is claimed is:

1. A method for heat-setting a garment containing spandex to differing extents comprising the steps of:
   mounting the garment comprising a plurality of different parts on a boarding form;
   heating the mounted garment by subjecting the garment to a plurality of different preselected elevated temperatures corresponding spatially to the different parts so that the thermal histories of the different parts will be different; and
   removing the garment so heat-set from the form, the different parts of the garment exerting different compressive forces when the garment is worn.

2. The method of claim 1 wherein the garment is a pair of stockings or pantyhose.

3. The method of claim 2 wherein the elevated temperatures are in the range of about 40° C.–300° C.

4. The method of claim 3 wherein the garment is heated by dry heat; wherein the garment parts are foot, calf, knee and thigh, and the elevated temperatures for the plurality of parts of the stockings are in the range of about 100° C.–140° C. for the foot, about 110° C.–150° C. for the calf, about 130° C.–170° C. for the knee, and about 150° C.–200° C. for the thigh.

\* \* \* \* \*